United States Patent
Yoon et al.

(10) Patent No.: US 8,382,690 B2
(45) Date of Patent: Feb. 26, 2013

(54) PORTABLE PHYSIS-STIMULATING DEVICE FOR PROMOTING GROWTH WITH TWO-PHASE ULTRASONIC VIBRATION GENERATORS AND LED ELEMENTS

(75) Inventors: Taek Rim Yoon, Gwangju (KR); Sung Jun Park, Gwangju (KR); Hyung Keun Kim, Hwasoon-gun (KR); Dong Ok Kim, Gwangju (KR)

(73) Assignee: Industry Foundation of Chonnam National University (KR)

( * ) Notice: Subject to any disclaimer, the term of this patent is extended or adjusted under 35 U.S.C. 154(b) by 198 days.

(21) Appl. No.: 12/863,174

(22) PCT Filed: Jan. 15, 2009

(86) PCT No.: PCT/KR2009/000198
§ 371 (c)(1),
(2), (4) Date: Jul. 15, 2010

(87) PCT Pub. No.: WO2009/091181
PCT Pub. Date: Jul. 23, 2009

(65) Prior Publication Data
US 2011/0060254 A1    Mar. 10, 2011

(30) Foreign Application Priority Data
Jan. 15, 2008    (KR) .................. 10-2008-0004442

(51) Int. Cl.
*A61H 1/00*    (2006.01)
*A61B 6/00*    (2006.01)
(52) U.S. Cl. .................................. 601/2; 600/476
(58) Field of Classification Search ........ 601/2; 600/473, 600/476
See application file for complete search history.

(56) References Cited

U.S. PATENT DOCUMENTS

| 6,139,496 A | * | 10/2000 | Chen et al. ............... 600/437 |
| 2002/0188229 A1 | | 12/2002 | Ryaby et al. |

FOREIGN PATENT DOCUMENTS

| JP | 06-339538 | 12/1994 |
| JP | 06-339538 A | 12/1994 |
| JP | 2000-060929 | 2/2000 |
| JP | 2000-060929 A | 2/2000 |
| KR | 20-0225764 | 6/2001 |
| KR | 20-0225764 Y1 | 6/2001 |
| KR | 20-0267842 | 3/2002 |
| KR | 20-0267842 Y1 | 3/2002 |
| KR | 20-0350247 | 5/2004 |
| KR | 20-0350247 Y1 | 5/2004 |
| KR | 10-2006-0127281 | 1/2007 |
| KR | 10-2006-0127281 A | 1/2007 |
| KR | 10-2009-0078542 | 7/2009 |

* cited by examiner

*Primary Examiner* — Michael Rozanski
(74) *Attorney, Agent, or Firm* — John K. Park; Park Law Firm (57) ABSTRACT

Disclosed herein is a growth plate stimulation-type portable growth promotion apparatus including two-phase ultrasonic vibration generators and Light Emitting Diode (LED) devices. The ring-shaped two-phase ultrasonic vibration generators have a center hole. Each of the LED devices is provided in the center hole of the each two-phase ultrasonic vibration generator. The two-phase ultrasonic vibration generators includes a ring-shaped vibration stator configured to have a center hole; a first electrode layer provided under the vibration stator; a second electrode layer provided under the first electrode layer; and a piezoelectric ceramic group layer configured to include a first piezoelectric ceramic group for generating an A phase and a second piezoelectric ceramic group for generating a B phase. Growth plates are stimulated using two-phase ultrasound projected from the two-phase ultrasonic vibration generators and light projected from the LED devices.

8 Claims, 5 Drawing Sheets

PORTABLE PHYSIS-STIMULATING DEVICE FOR PROMOTING GROWTH WITH TWO-PHASE ULTRASONIC VIBRATION GENERATORS AND LED ELEMENTS

TECHNICAL FIELD

The present invention relates, in general, to a growth plate stimulation-type portable growth promotion apparatus including two-phase ultrasonic vibration generators and Light Emitting Diode (LED) devices, and, more particularly, to an apparatus capable of promoting the cultivation and specialization of the cartilage cells of growth plates by stimulating the growth plates using two-phase ultrasonic vibration generators and LED devices.

BACKGROUND ART

Ultrasound was originally developed for military purposes, has widely used for industrial and medical purposes, and has been chosen for therapy and beauty purposes because of the advantage of there being no side effects and no harm resulting when properly adjusted ultrasound is used on the human body.

Ultrasound is the physical and ultra speed vibration of sound that is safe, and transfers extremely delicate vibration from the surface of the skin to cell units deep in the tissue depending on the strength settings and the time of application, thereby imparting the effects of a micro massage. Furthermore, proteins, polysaccharides, and fat are decomposed due to the minute friction and catabolism (living creatures obtain the life energy they require in such a way that materials taken from the outside are chemically decomposed in the body and are reacted upon by simple materials) between molecules, thereby generating heat.

Therefore, the temperature of cells and tissues instantaneously rises, so that a natural convection phenomenon wherein blood flows from the circumference in order to reduce the temperature of the hot place, thereby promoting the functions of blood circulation and metabolism.

Meanwhile, with regard to optical treatment, the medical treatment team at the University of Wisconsin-Madison located in Milwaukee discovered a light source which has healing power capable of helping the space shuttle operating techniques of the National Aeronautics and Space Administration (NASA) of the United states, and it has been made clear that, if strong LEDs which were developed to cultivate marketable crops in space is used for medical purposes, it is helpful in healing patients in space as well as on Earth.

However, although some medical instruments and instruments offering medical aid that use ultrasound and LEDs according to the conventional art have been released and used, there has been no introduction of a technique for stimulating growth plates by combining the two techniques.

DISCLOSURE

Technical Problem

Accordingly, the present invention has been made keeping in mind the above problems occurring in the prior art, and an object of the present invention is to provide a growth plate stimulation-type portable growth promotion apparatus, which stimulates growth plates by mixedly projecting ultrasound and LED light thereto, thereby promoting the cultivation and specialization of the cartilage cells of the growth plates, and ultimately aiding the growth and development of the human body.

Another object of the present invention is to provide a growth plate stimulation-type portable growth promotion apparatus, which uses two-phase traveling wave-type ultrasound generators unlike conventional ultrasound generators, so that the phases can be set to be ±90° and 0, with the result that ultrasound is projected in two modes, thereby increasing the effect of stimulating growth plates.

A further object of the present invention is to provide a growth plate stimulation-type portable growth promotion apparatus, which brings the heat generated by two-phase ultrasonic vibration generators into growth plates, thereby imparting a thermal effect.

Yet another object of the present invention is to provide a growth plate stimulation-type portable growth promotion apparatus, which includes LED devices, so that radiation of the infrared wave band which is effective in medical treatment can be performed, thereby enabling effective photochemical treatment.

Still another object of the present invention is to provide a growth plate stimulation-type portable growth promotion apparatus, which is simply configured to include a promoter body and a controller body, so that it can be easy to carry, thereby allowing it to be used easily without being subject to space limitations.

Technical Solution

In order to accomplish the above objects, the present invention provides a growth plate stimulation-type portable growth promotion apparatus including two-phase ultrasonic vibration generators and Light Emitting Diode (LED) devices, including: a plurality of ring-shaped two-phase ultrasonic vibration generators each configured to have a center hole; and a plurality of LED devices each provided in the center hole of the each two-phase ultrasonic vibration generator; wherein each of the two-phase ultrasonic vibration generators includes: a ring-shaped vibration stator configured to have a center hole; a first electrode layer provided under the vibration stator; a second electrode layer provided under the first electrode layer; and a piezoelectric ceramic group layer provided between the first electrode layer and the second electrode layer, configured to correspond to the ring shape of the vibration stator, and configured to include a first piezoelectric ceramic group for generating an A phase and a second piezoelectric ceramic group for generating a B phase; wherein growth plates are stimulated using two-phase ultrasound projected from the two-phase ultrasonic vibration generators and light projected from the LED devices.

Further, the present invention provides a growth plate stimulation-type portable growth promotion apparatus further including: a promoter body configured to include a head which has a bottom surface and a cover, and a grip which extends from the head; the plurality of ring-shaped two-phase ultrasonic vibration generators each provided on the bottom surface of the head, configured to generate the A phase and the B phase, and configured to have the center hole; the plurality of LED devices provided in the center hole of each of the two-phase ultrasonic vibration generators; and a first display unit and a first input unit provided on the cover of the head, and connected to the two-phase ultrasonic vibration generators and the LED devices.

In a preferred embodiment, each of the two-phase ultrasonic vibration generators includes: an A-phase vibration device configured to include the first piezoelectric ceramic group which generates the A phase, and electrodes which are provided on the upper and lower portions of the first piezoelectric ceramic group and which are configured to supply power to the first piezoelectric ceramic group; a B-phase vibration device configured to include the second piezoelectric ceramic group which generates the B phase, and electrodes which are provided on the upper and lower portions of the second piezoelectric ceramic group and which are configured to supply power to the second piezoelectric ceramic group; and the vibration stator provided on the A-phase vibration device and the B-phase vibration device, and configured to transfer the A-phase and the B-phase respectively generated by the A-phase vibration device and the B-phase vibration device to an outside.

In a preferred embodiment, a first connection terminal is provided on one side of the promoter body in order to connect the first input unit, the first display unit, the ultrasonic vibration generators, and the LED devices to the outside.

In a preferred embodiment, the growth plate stimulation-type portable growth promotion apparatus further includes a controller body including a second connection terminal connected to the first connection terminal using a connection cable; wherein the controller body includes: a power supply device provided therein; a control unit connected to the power supply device, and connected to the first input unit, the first display unit, the two-phase ultrasonic vibration generators and the LED devices of the promoter body through the second connection terminal; and a second input unit and a second display unit connected to the control unit.

In a preferred embodiment, the first input unit is an input unit for inputting a signal used to control the strength of each of the two-phase ultrasonic vibration generators and each of the LED devices; the first display unit is a display unit for displaying the operational time of the growth plate stimulation-type portable growth promotion apparatus; the second input unit is an input unit for inputting a signal used to control the operational mode of the growth plate stimulation-type portable growth promotion apparatus; and the second display unit is a display unit for displaying signals provided from the control unit.

Advantageous Effects

The growth plate stimulation-type portable growth promotion apparatus including two-phase ultrasonic vibration generators and LED devices according to the present invention has the following advantages:

First, according to the growth plate stimulation-type portable growth promotion apparatus of the present invention, growth plates are stimulated by mixedly projecting ultrasound and LED light thereto, thereby promoting the cultivation and specialization of the cartilage cells of the growth plates, and ultimately aiding the growth and development of the human body.

Further, according to the growth plate stimulation-type portable growth promotion apparatus of the present invention, two-phase traveling wave-type ultrasound generators are used unlike conventional ultrasound generators, so that the phases can be set to be ±90° and 0, with the result that ultrasound is projected in two modes, thereby increasing the effect of stimulating growth plates.

Further, according to the growth plate stimulation-type portable growth promotion apparatus of the present invention, the growth plate stimulation-type portable growth promotion apparatus including two-phase ultrasonic vibration generators and LED devices brings the heat generated by two-phase ultrasonic vibration generators into growth plates, thereby using a thermal effect.

Further, according to the growth plate stimulation-type portable growth promotion apparatus of the present invention, LED devices are included therein, so that radiation of the infrared wave band which is effective in medical treatment can be performed, thereby enabling effective photochemical treatment.

Further, according to the growth plate stimulation-type portable growth promotion apparatus of the present invention, the growth plate stimulation-type portable growth promotion apparatus includes a simple configuration of a promoter body and a controller body, so that it can be easy to carry, thereby allowing it to be used easily without being subject to space limitations.

| <Description of reference numerals of principle elements in the drawings> | |
|---|---|
| 100 | two-phase ultrasonic vibration generator |
| 200 | LED device |
| 300 | head of promoter body |
| 400 | grip of promoter body |
| 500 | controller body |
| 600 | connecting cable |

BEST MODE

The details of the above objects, technical configurations, and effects according to the present invention will be clearly understood from the following detailed description taken in conjunction with the accompanying drawings showing preferred embodiments of the present invention. Further, in the drawings, the length and thickness of layers and areas may be exaggerated for the sake of convenience. Reference should now be made to the drawings, in which the same reference numerals are used throughout the different drawings to designate the same components.

Figure 1:
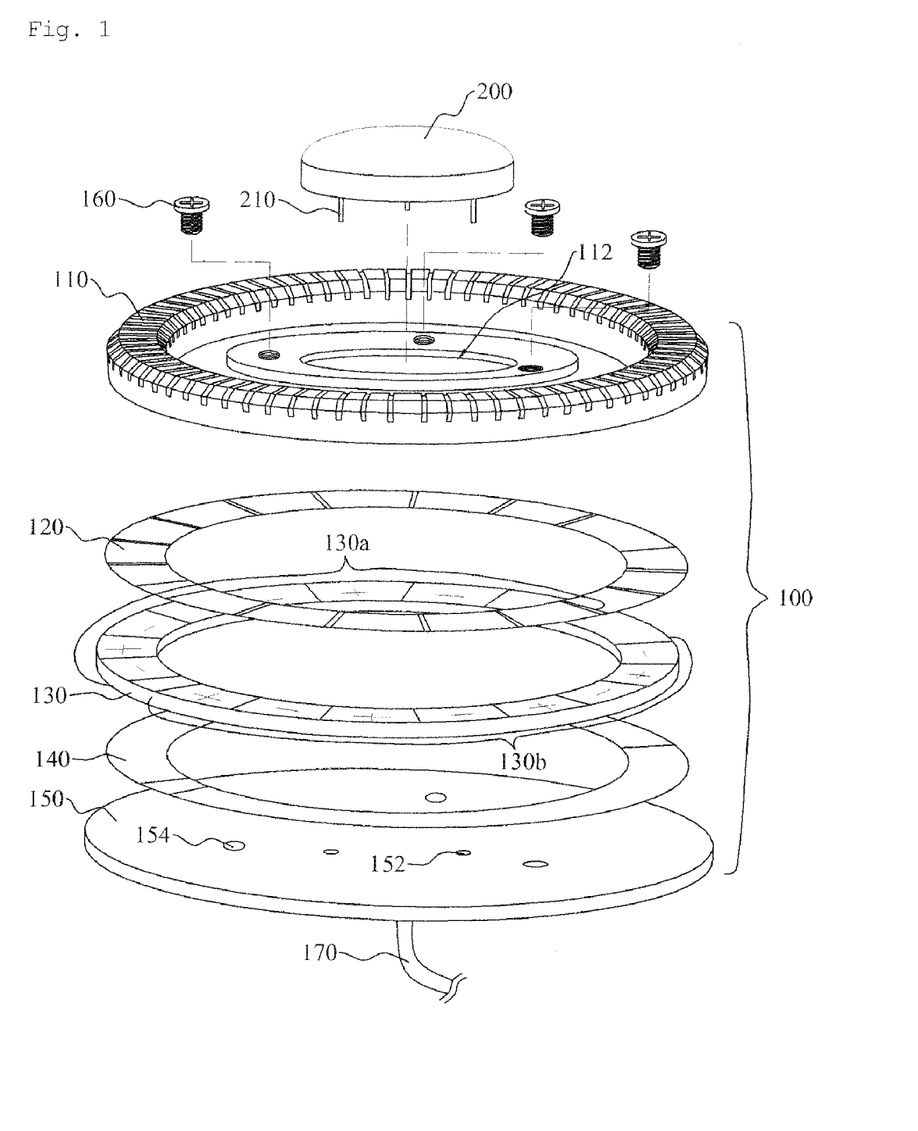
FIG. 1 is a perspective view showing the two-phase ultrasonic vibration generator and LED device of a growth plate stimulation-type portable growth promotion apparatus including two-phase ultrasonic vibration generators and LED devices according to an embodiment of the present invention.

FIG. 1 is a perspective view showing the two-phase ultrasonic vibration generator and LED device of a growth plate stimulation-type portable growth promotion apparatus including two-phase ultrasonic vibration generators and LED devices according to an embodiment of the present invention.

Referring to FIG. 1, the growth plate stimulation-type portable growth promotion apparatus according to the present invention includes a plurality of two-phase ultrasonic vibration generators 100 and a plurality of LED devices 200.

Each of the two-phase ultrasonic vibration generators 100 generates an A phase and a B phase, and is a ring-shaped two-phase ultrasonic vibration generator which has a center hole 112.

Here, each of the LED devices 200 is provided in the center hole 112. Here, the LED device 200 is a device for projecting light in the infrared wavelength band. Here, the infrared wavelength band means an infrared wavelength band of at least 680 nm or more.

The two-phase ultrasonic vibration generator 100 may include a vibration stator 110, a first electrode layer 120, a piezoelectric ceramic layer 130, a second electrode layer 140, and a bottom plate 150.

The vibration stator 110 functions to transfer ultrasound generated at the bottom.

The first electrode layer 120 and the second electrode layer 140 function to supply power to the piezoelectric ceramic layer 130.

Here, as shown in FIG. 1, the piezoelectric ceramic layer 130 includes a first piezoelectric ceramic group 130a configured to include a plurality of piezoelectric ceramic segments which generate an A phase, and a second piezoelectric ceramic group 130b configured to include a plurality of piezoelectric ceramic segments which generate a B phase.

The first piezoelectric ceramic group 130a and the second piezoelectric ceramic group 130 are configured to respectively occupy half of the ring shape.

Therefore, the two-phase ultrasonic vibration generator 100 of the present invention includes an A-phase vibration device configured to include the first piezoelectric ceramic group 130a which generates the A phase and electrodes which are provided on the upper and lower portions of the first piezoelectric ceramic group 130a and which supply power to the first piezoelectric ceramic group 130a, and includes a B-phase vibration device configured to include the second piezoelectric ceramic group 130b which generates the B phase and electrodes which are provided on the upper and lower portions of the second piezoelectric ceramic group 130b and which supply power to the second piezoelectric ceramic group 130b, thereby generating two-phase ultrasound. The operations of the A-phase vibration device and the B-phase vibration device will be described in detail with reference to FIGS. 2 and 3.

The bottom plate 150 functions to fasten and fix the vibration stator 110, the first electrode layer 120, the piezoelectric ceramic layer 130, and the second electrode layer 140.

That is, fastening members 160, such as screws, enable the vibration stator 110 to be fixed into the screw fastening member 152 of the bottom plate 150, so that each of the elements of the two-phase ultrasonic vibration generator 100 is fixed into the bottom plate 150.

Further, the bottom plate 150 includes LED electrode fastening members 154 for fastening the electrodes 210 of the LED device 200 so that the LED device 200 is fastened to the two-phase ultrasonic vibration generator 100.

Further, the bottom plate 150 includes a power supply line 170 for supplying power to the first electrode layer 120, the second electrode layer 140, and the electrodes 210 of the LED device 200.

Therefore, the portable and complex physical therapy device including two-phase ultrasonic vibration generators and LED devices according to the embodiment of the present invention includes a plurality of two-phase ultrasonic vibration generators 100 and a plurality of LED devices, so that ultrasound projected from the two-phase ultrasonic vibration generators 100 and the infrared waves projected from the LED devices 200 can be simultaneously projected to the growth plates, thereby promoting the cultivation and specialization of the cartilage cells of the growth plates.

Here, each two-phase ultrasonic vibration generator 100 can use two modes, that is, a traveling wave vibration stimulation in which the motion of a certain particle on the surface of the vibration stator 110 is an ellipse and a standing wave vibration stimulation in which the motion of a particle on the surface is straight line, so that various types of vibration stimulations can be projected onto growth plates, thereby realizing excellent effects.

Further, a thermal effect may be expected using the heat generated from the two-phase ultrasonic vibration generator 100 itself.

Figure 2:
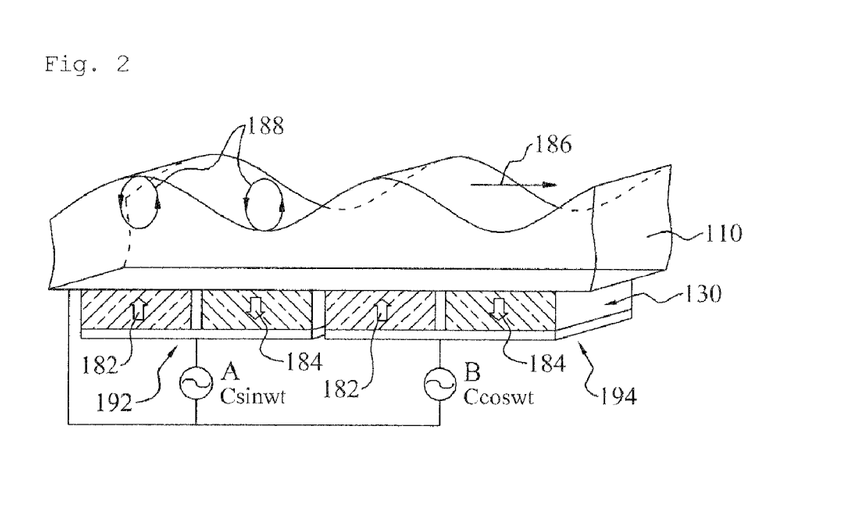
FIGS. 2 and 3 are conceptual diagrams showing the two-phase ultrasonic vibration generator according to the embodiment of the present invention.
Figure 3:
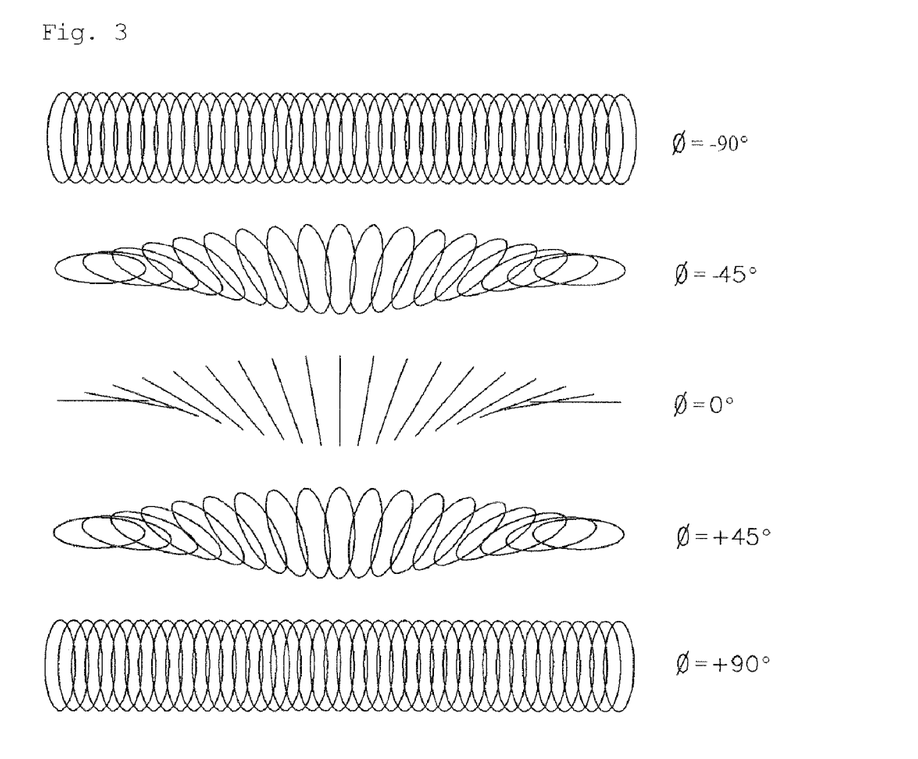

FIGS. 2 and 3 are conceptual diagrams showing the two-phase ultrasonic vibration generator according to the embodiment of the present invention.

Referring to FIGS. 2 and 3, in the two-phase ultrasonic vibration generator, when a sine wave electric field is applied in the thickness direction of the piezoelectric ceramic layer 130, mechanical extension 182 and contraction 184 are generated depending on the polarization direction of piezoelectric materials, as shown in FIG. 2.

Such extension 182 and contraction 184 of the piezoelectric ceramic layer 130 appear on the surface of the vibration stator 110 in the form of standing waves.

Here, when the phase difference is ±90°, the standing waves generated on respective phases are composed inside the vibration stator 110 and the traveling waves 186 appear on the surface of the vibration stator 110 in the form of traveling waves 186.

Here, the motion of a certain particle on the surface of the vibration stator 110 is elliptical motion 188, and the speed and torque of the ultrasonic vibration generator can be controlled by adjusting the size, shape, and direction of rotation of the ellipses 188.

First, a method of adjusting the phase difference of the two-phase ultrasonic vibration generator of the present invention will be described.

As shown in FIG. 2, when sine wave voltage is applied individually to the A-phase vibration device 192 for generating the A-phase and the B-phase vibration device 194 for generating the B-phase, standing waves are generated for the respective phases.

The phase difference between the spatial phase of the standing waves generated by the A-phase vibration device 192 and the spatial phase generated by the B-phase vibration device 194 is 90° based on the configuration of the two-phase ultrasonic vibration generator.

Further, when a sine wave power of Φ is timely supplied to the A-phase vibration device 192 and the B-phase vibration device 194, the standing waves which are the waves of mechanical vibration generated by the A-phase vibration device 192 and the B-phase vibration device 194 can be expressed by the following Equations 1 and 2:

$$Y_A = \varsigma_A \sin(nx)\sin(\omega_0 t) \quad (1)$$

$$Y_B = \varsigma_B \sin(nx + \pi/2)\sin(\omega_0 t + \Phi) \quad (2)$$
$$= \varsigma_B \cos(nx)\sin(\omega_0 t + \Phi)$$

where $\varsigma_A$ and $\varsigma_B$ indicate integral numbers, x indicates a location on the circumference, and n indicates the number of standing waves on the circumference.

Since the standing waves generated by the A-phase vibration device 192 and the B-phase vibration device 194 are composed inside the same vibration stator 110, Equations 1 and 2 may be readjusted into the following Equation 3:

$$Y = \varsigma_A \sin(nx)\sin(\omega t) + \varsigma_B \cos(nx)\sin(\omega t + \Phi) \quad (3)$$

where if it is assumed that $\varsigma_B = \varsigma_A \times \gamma$, that is, it is assumed that the amplitude is $\gamma = \varsigma_B/\varsigma_A$, Equation 3 is expressed by the following Equation 4:

$$Y = \varsigma_A\{\sin(nx)\sin(\omega t) + \gamma \cos(nx)\sin(\omega t + \Phi)\} \quad (4)$$

The mechanical vibration attributable to the traveling waves corresponds to the neutral plane at the center of the thickness T of the vibration stator 130, and the displacement X in a circumferential direction and the displacement Y in an axial direction which are on the surface of the vibration stator 130 and which are apart from the neutral plane by T/2 may be respectively expressed by the following Equations 5 and 6:

$$X = x - \frac{T}{2}\sin\theta \approx x - \frac{T}{2}\tan\theta \quad (5)$$
$$(\theta \approx 0, \sin\theta \approx \tan\theta = \theta)$$

$$Y = y + \frac{T}{2}\cos\theta \approx y + \frac{T}{2} \quad (6)$$
$$(\cos\theta \approx 1)$$

where $\tan\theta$ of Equation 5 can be expressed by the following Equation 7:

$$\tan\theta = \frac{\partial y}{\partial x} = n\varsigma_A\{\cos(nx)\sin(\omega t) - \gamma\sin(nx)\sin(\omega t + \phi)\} \quad (7)$$

where if Equation 4 and Equation 7 are substituted for Equation 6 and Equation 5, the results may be expressed as the following Equation 8 and Equation 9:

$$X = x - \frac{nT\varsigma_A}{2} = \{\cos(nx)\sin(\omega t) - \gamma\sin(nx)\sin(\omega t + \phi)\} \quad (8)$$

$$Y = \frac{T}{2} + \varsigma_A\{\sin(nx)\sin(\omega t) - \gamma\cos(nx)\sin(\omega t + \phi)\} \quad (9)$$

The equation of an ellipse generated on the surface of the vibration stator 110 may be obtained using Equation 8 and Equation 9 and may be expressed as the following Equation 10:

$$A(X-x)^2 + B(X-x)\left(Y - \frac{T}{2}\right) + C\left(Y - \frac{T}{2}\right)^2 = 1 \quad (10)$$

where A, B, and C of Equation 10 are $$A = \left(\frac{2\cos(nx)}{nT}\right)^2 (P^2 + Q^2)\left(\frac{1}{\varsigma_A^2 Q^2}\right)$$

$$B = \left(\frac{P}{nT}\right)\cos(nx)\left(1 - \sin(nx)(P^2 + Q^2)\left(\frac{1}{\varsigma_A^2 Q^2}\right)\right),$$

$$C = (P\sin(nx) - 1)^2 + \sin^2(nx)Q^2\left(\frac{1}{\varsigma_A^2 Q^2}\right)$$

P and Q are
$$P = \sin(nx) + \gamma \cos(nx)\cos\phi,$$

and $$Q = -\gamma \cos(nx)\sin\phi$$

and a, b, and $\theta_R$ are $$a = \sqrt{\frac{2}{(A+C) - \sqrt{(A-C)^2 + B^2}}}$$

$$b = \sqrt{\frac{2}{(A-C) - \sqrt{(A-C)^2 + B^2}}}$$

$$\theta_R = \frac{1}{2}\tan^{-1}\frac{B}{A-C}.$$

Therefore, Equation 10 expresses an ellipse the center of which is (x,T/2), the long axis of which is a, the short axis of which is b, and the rotation of which is $\theta_R$.

Here, as shown in FIG. 3, if $\phi$ is changed from $-90°$ to $0°$, the vibration generated in the vibration stator 110 is sequentially changed from the traveling waves in the counterclockwise direction to the standing waves, and, when $\phi$ is $0°$, the traveling waves are entirely changed into the standing waves, and the operation of the two-phase ultrasonic vibration generator stops.

When $\phi$ is changed from $0°$ into $+90°$, the standing waves are changed into traveling waves in the clockwise direction.

Here, the distribution of the standing waves and traveling waves gradually changes depending on the value of $\phi$, and the traveling waves are referred to as bending traveling waves when $\phi$ is between $-90°$ and $0°$ or between $0°$ and $+90°$.

Therefore, the principle of adjusting the phase difference is configured such that the phase difference of the input voltage of the A-phase vibration device 192 and the B-phase vibration device 194 is adjusted, the phase difference parameter $\phi$ of the Equation of an ellipse, obtained using Equation 10, is changed so that the long axis, short axis, the direction of rotation, and gradient of the ellipse are changed, so that the strength, kind, and direction of the vibration generated by the two-phase ultrasonic vibration generator can be controlled.

Therefore, the two-phase ultrasonic vibration generator according to the present invention can use the motion at a certain particle on the surface of the vibration stator 110 in two modes, that is, the traveling waves, the motion at the certain particle of which is an ellipse, and the standing waves, the motion at the certain particle of which is a straight line, using the principle of adjusting the phase difference.

Next, a method of adjusting the frequency of the two-phase ultrasonic vibration generator will be described below.

Generally, the ultrasonic vibration generator generates the greatest torque when a mechanical resonance frequency is identical with the electric resonance frequency of a power conversion device, that is, the frequency of input power. The mechanical resonance frequency changes depending on temperature and load, and the speed thereof gradually decreases as the temperature increases.

This fact shows that the mechanical resonance frequency moves to a frequency band where the optimum resonance point is low.

Generally, the frequency of the two-phase ultrasonic vibration generator is adjusted by decreasing the electric resonance frequency, that is, the frequency of the input power.

However, if the frequency is reduced even when the optimum resonance point is being passed, the speed of the ultrasonic vibration generator rapidly decreases and then the ultrasonic vibration generator stops.

Driving the electric resonance frequency of the power conversion device can be efficient and the stable operational point of the electric resonance frequency of the power conversion device can be found only when the changed mechanical resonance frequency of the ultrasonic vibration generator is ascertained and used.

In order to show the mechanical resonance frequency of the ultrasonic vibration generator, the mechanical constants of the two-phase ultrasonic vibration generator of the present invention are expressed by the following Equation 11. Here, $L_{usm}$ indicates an equivalent inductor attributable to a vibration stator mass effect and $C_{usm}$ indicates a capacitor attributable to a vibration stator spring effect.

$$L_{usm} = \frac{m}{F^2} \quad (11)$$
$$C_{usm} = \frac{F^2}{K}$$

where m indicates the mass of the ceramic and metal of the vibration stator, F indicates a force factor, and K indicates the spring constant between the ceramic and metal of the vibration stator.

The mechanical resonance frequency $f_{usm}$ of the two-phase ultrasonic vibration generator using the mechanical constants is expressed by the following Equation 12:

$$f_{usm} = \frac{1}{2\pi}\sqrt{\frac{1}{C_{usm}L_{usm}}} = \frac{1}{2\pi}\sqrt{\frac{K}{m}} \quad (12)$$

Therefore, the frequency $f_s$ of the power supply voltage directly applied to the two-phase ultrasonic vibration generator of the present invention is expressed by the following Equation 13:

$$f_s = \frac{1}{2\pi}\sqrt{\frac{1}{C_d L_i}} = \Delta f \quad (13)$$

where $C_d$ indicates piezoelectric ceramic blocking capacitance of the piezoelectric ceramic layer 130 of the two-phase ultrasonic vibration generator, and $L_i$ indicates external inductance, and $\Delta f$ indicates the variable frequency which is necessary to control the two-phase ultrasonic vibration generator.

Therefore, the frequency of the power supply voltage that can be used to generate the greatest torque of the two-phase ultrasonic vibration generator of the present invention can be ascertained using Equation 13.

MODE FOR INVENTION

Figure 4:
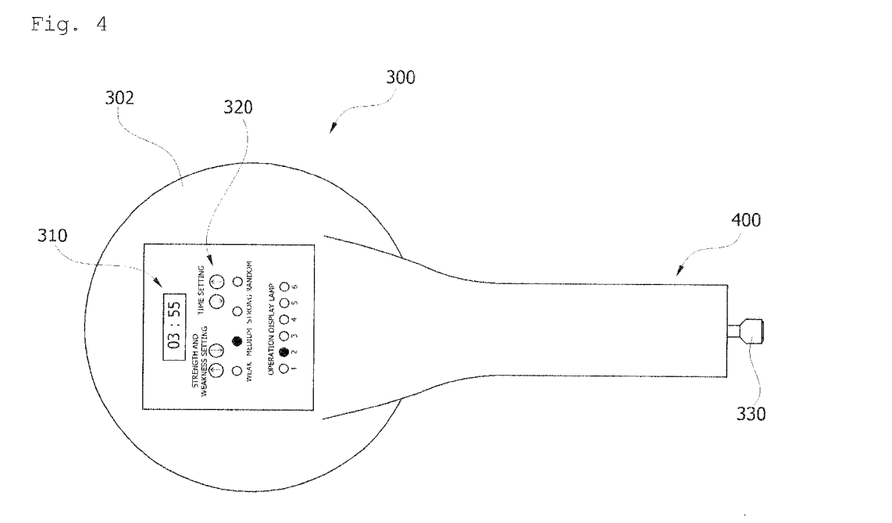
FIGS. 4 to 6 are views showing the top, bottom, and side of the promoter body of the growth plate stimulation-type portable growth promotion apparatus including two-phase ultrasonic vibration generators and LED devices according to the embodiment of the present invention.
Figure 5:
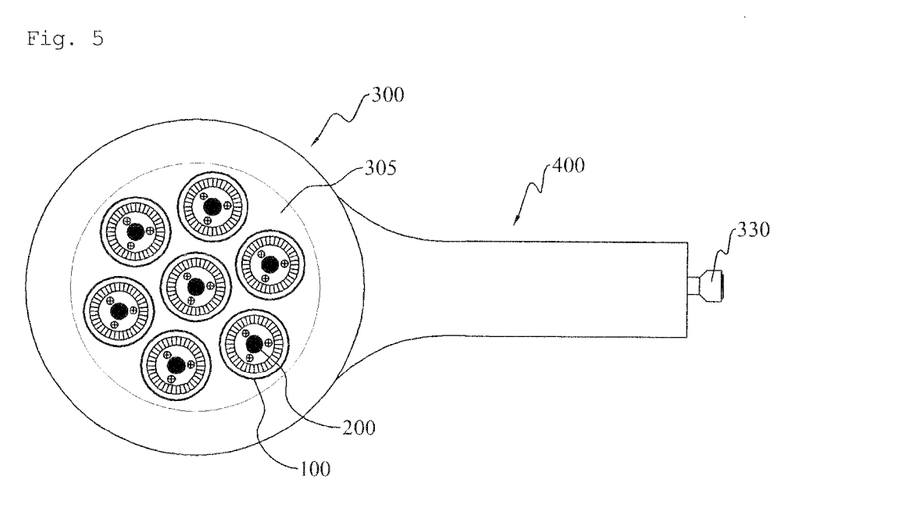
Figure 6:
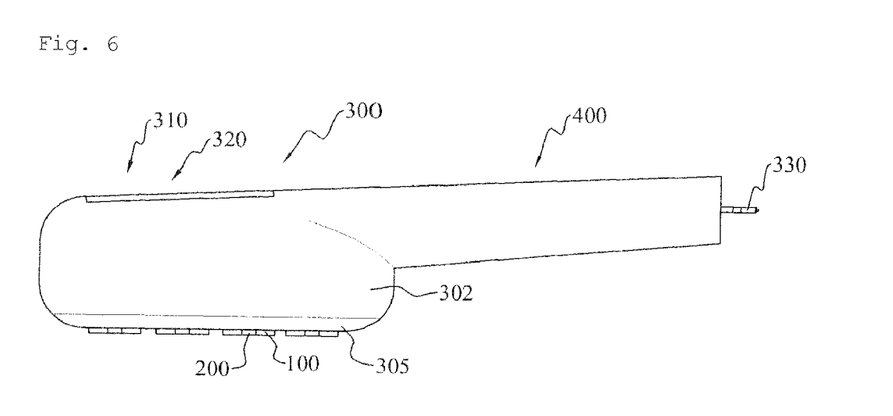

FIGS. 4 to 6 are views showing the top, bottom, and side of the promoter body of the growth plate stimulation-type portable growth promotion apparatus including two-phase ultrasonic vibration generators and LED devices according to the embodiment of the present invention.

Referring to FIGS. 4 to 6, the promoter body of the growth plate stimulation-type portable growth promotion apparatus including the two-phase ultrasonic vibration generators and LED devices according to an embodiment of the present invention includes a head 300 and a grip 400.

Here, the grip 400 is provided for a user, who uses the growth plate stimulation-type portable growth promotion apparatus, to easily grip the promoter body, and concavities and convexities may be provided on the surface thereof although not shown in the drawings in detail.

On a predetermined location of the cover 302 of the head 300 of the promoter body, a first display unit 310 for displaying the operation time of the growth plate stimulation-type portable growth promotion apparatus and a first input unit 320 for enabling a user to input the strength/weakness and time of the operation of the growth plate stimulation-type portable growth promotion apparatus are provided.

A plurality of two-phase ultrasonic vibration generators 100 including the LED devices 200, which have been described with reference to FIG. 1, are attached to the bottom surface 305 of the head 300 of the promoter body.

Here, although the shape of the bottom surface 305 is shown in FIGS. 5 and 6 as being planar, there is no problem if the shape of the bottom surface 305 is provided in a hemispherical shape swollen in a downward direction. That is, the bottom surface 305 is provided to have the shape which enables the two-phase ultrasound and LED light to be easily projected on growth plates.

The grip 400 includes a first connection terminal 330 at one end thereof, the first connection terminal 330 being provided to connect the first display unit 310, the first input unit 320, the two-phase ultrasonic vibration generators 100, and the LED devices 200 to the outside, such as a controller body which will be described later.

Therefore, the growth plate stimulation-type portable growth promotion apparatus including two-phase ultrasonic vibration generators and LED devices of the present invention includes two-phase ultrasonic vibration generators and LED devices, and stimulates growth plates using ultrasound and light projected by the two-phase ultrasonic vibration generators and the LED devices, thereby ultimately aiding the growth and development of a human body.

Figure 7:
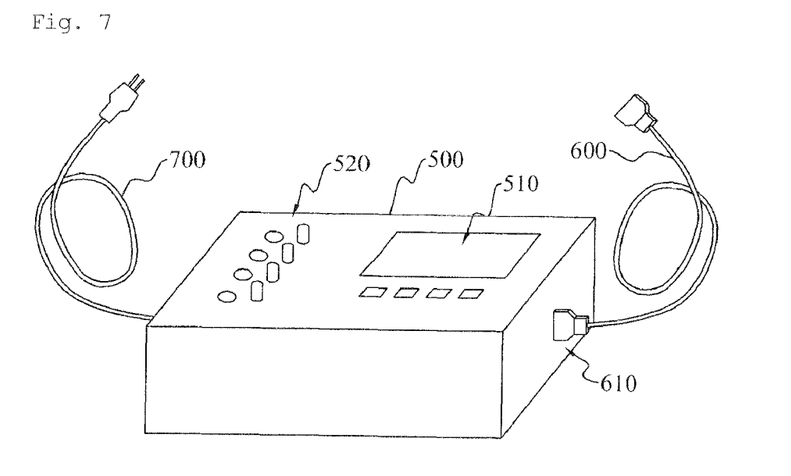
FIG. 7 is a view showing the controller body of the growth plate stimulation-type portable growth promotion apparatus including two-phase ultrasonic vibration generators and LED devices according to the embodiment of the present invention.

FIG. 7 is a view showing the controller body of the growth plate stimulation-type portable growth promotion apparatus including two-phase ultrasonic vibration generators and LED devices according to the embodiment of the present invention.

Referring to FIG. 7, the controller body 500 of the growth plate stimulation-type portable growth promotion apparatus including two-phase ultrasonic vibration generators and LED devices includes a second connection terminal 610 connected to the first connection terminal 330 of the promoter body 300 using the connection cable 600.

Further, although not shown in the drawing in detail, the controller body 500 includes a power supply device which includes a power conversion device, and a control unit which is connected to the first display unit 310, the first input unit 320, the two-phase ultrasonic vibration generators 100, and the LED devices 200 of the head 300 fo the therapy device body 300 using the connection cable 600.

Here, the power supply device functions to convert the power supplied from the outside into a Direct Current (DC) of 24 V or 12 V, and to provide the resulting DC to the growth plate stimulation-type portable growth promotion apparatus of the present invention.

Further, a second display unit 510 is provided on the surface of the controller body 500, the second display unit 510 being connected to the control unit, and configured to display signals provided from the control unit, for example, the setting mode of the two-phase ultrasonic vibration generators.

Further, a second input unit 520 is provided on the surface of the controller body 500, the second input unit 520 being configured to receive signals used to control the operational mode of the two-phase ultrasonic vibration generator, such as the frequency, duty ratio, and phase difference of ultrasound, and signals used to control the strength of the LED devices.

Meanwhile, the controller body 500 includes a power cable 700 used to supply external power, and supplies power to the controller body 500.

Therefore, as described above, the growth plate stimulation-type portable growth promotion apparatus including two-phase ultrasonic vibration generators and LED devices of the present invention is designed to include the promoter body and the controller body so that it can be easily carried and used.

Figure 8:
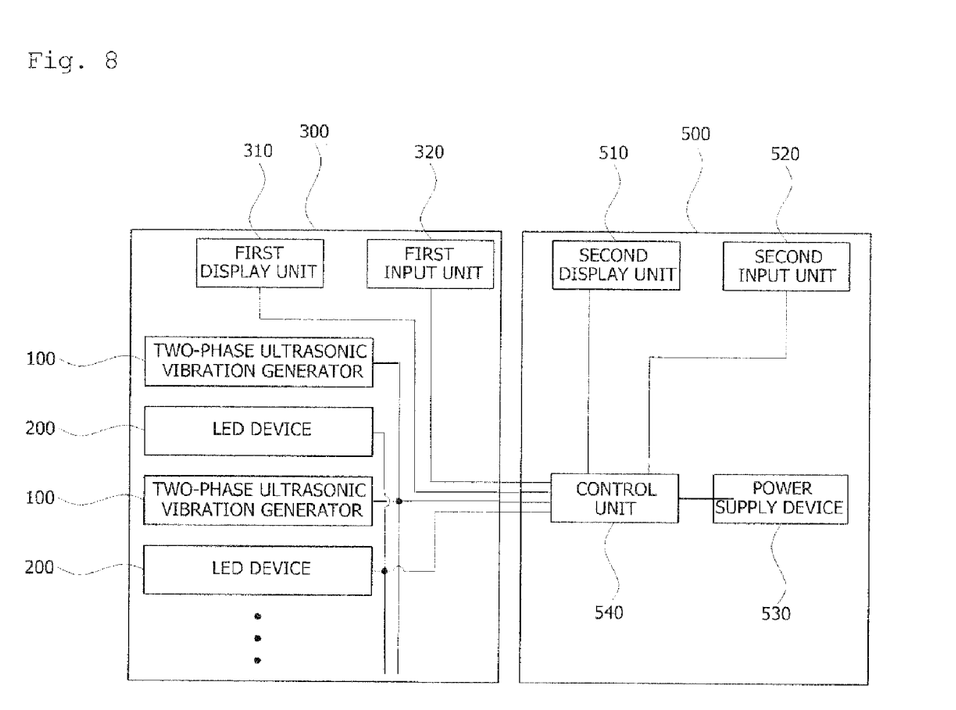
FIG. 8 is a circuit view showing the circuit of the entire growth plate stimulation-type portable growth promotion apparatus including two-phase ultrasonic vibration generators and LED devices according to the embodiment of the present invention.

FIG. 8 is a circuit view showing the circuit of the entire growth plate stimulation-type portable growth promotion apparatus including two-phase ultrasonic vibration generators and LED devices according to an embodiment of the present invention.

Referring to FIG. 8, the growth plate stimulation-type portable growth promotion apparatus including two-phase ultrasonic vibration generators and LED devices includes the promoter body 300 and the controller body 500.

The promoter body 300 includes the first display unit 310, the first input unit 320, the two-phase ultrasonic vibration generators 100, and the LED devices 200.

Further, the controller body 500 includes the second display unit 510, the second input unit 520, the power supply device 530 having the power conversion device, and the control unit 540.

Here, the control unit 540 is connected to the first display unit 310, the first input unit 320, the two-phase ultrasonic vibration generators 100, and the LED devices 200 of the promoter body 300 using the connection cable 600, and is connected to the second display unit 510 and the second input unit 520, which are provided on the surface of the controller body 500, and the power supply device 530.

Therefore, the control unit 540 processes various kinds of control signals input by a user through the first input unit 320 and the second input unit 520. The control unit 540 includes a microprocessor (not shown), and controls the two-phase ultrasonic vibration generators 100 and the LED devices 200 of the promoter body 300 by processing the control signals, and then displays the control signals and the results of the processing on the first display unit 310 and the second display unit 510.

The growth plate stimulation-type portable growth promotion apparatus including two-phase ultrasonic vibration generators and LED devices as described above stimulates growth plates by mixedly projecting ultrasound and LED light to the growth plates, thereby promoting the cultivation and specialization of the cartilage cells of the growth plates, and ultimately aiding the growth and development of the human body.

Two-phase traveling wave-type ultrasound generators are used unlike conventional ultrasound generators, so that the phases can be set to be ±90° and 0, with the result that ultrasound is projected in two modes, thereby increasing the effect of stimulating growth plates.

Further, the heat generated by two-phase ultrasonic vibration generators is brought into the growth plates of a patient, so that the growth plate stimulation-type portable growth promotion apparatus can be used for thermal treatment, and LED devices are included in the growth plate stimulation-type portable growth promotion apparatus, so that radiation of the infrared wave band which is effective in medical treatment can be performed, thereby enabling effective photochemical treatment.

INDUSTRIAL APPLICABILITY

Although the present invention has been illustrated and disclosed using the preferred embodiments as described above, the present invention is not limited thereto, and various modifications and substitutions are possible by those skilled in the art, without departing from the spirit of the present invention.

The invention claimed is:
1. A growth plate stimulation-type portable growth promotion apparatus including two-phase ultrasonic vibration generators and Light Emitting Diode (LED) devices, comprising:
  a promoter body configured to include a head which has a bottom surface and a cover, and a grip which extends from the head;
  a plurality of ring-shaped two-phase ultrasonic vibration generators each provided on the bottom surface of the head, configured to generate an A phase and a B phase, and configured to have a center hole;
  a plurality of LED devices provided in the center hole of each of the two-phase ultrasonic vibration generators; and
  a first display unit and a first input unit provided on the cover of the head, and connected to the two-phase ultrasonic vibration generators and the LED devices,
  wherein a phase difference between a spatial phase of the generated A phase and the spatial phase of the generated B phase is 90°.

2. The growth plate stimulation-type portable growth promotion apparatus according to claim 1, wherein each of the two-phase ultrasonic vibration generators comprises:
  an A-phase vibration device configured to include a first piezoelectric ceramic group which generates the A phase, and electrodes which are provided on upper and lower portions of the first piezoelectric ceramic group and which are configured to supply power to the first piezoelectric ceramic group;
  a B-phase vibration device configured to include a second piezoelectric ceramic group which generates the B phase, and electrodes which are provided on upper and lower portions of the second piezoelectric ceramic group and which are configured to supply power to the second piezoelectric ceramic group; and
  a vibration stator provided on the A-phase vibration device and, the B-phase vibration device, and configured to transfer the A-phase and the B-phase respectively generated by the A-phase vibration device and the B-phase vibration device to an outside.

3. The growth plate stimulation-type portable growth promotion apparatus according to claim 2, further comprising a first connection terminal provided on one side of the promoter body in order to connect the first input unit, the first display unit, the ultrasonic vibration generators, and the LED devices to the outside.

4. The growth plate stimulation-type portable growth promotion apparatus according to claim 3, further comprising a controller body including a second connection terminal connected to the first connection terminal using a connection cable; wherein the controller body comprises: a power supply device provided therein; a control unit connected to the power supply device, and connected to the first input unit, the first display unit, the two-phase ultrasonic vibration generators and the LED devices of the promoter body through the second connection terminal; and a second input unit and a second display unit connected to the control unit.

5. The growth plate stimulation-type portable growth promotion apparatus according to claim 4, wherein the first input unit is an input unit for inputting a signal used to control a strength of each of the two-phase ultrasonic vibration generators and each of the LED devices,
wherein the first display unit is a display unit for displaying operational time of the growth plate stimulation-type portable growth promotion apparatus,
wherein the second input unit is an input unit for inputting a signal used to control an operational mode of the growth plate stimulation-type portable growth promotion apparatus, and
wherein the second display unit is a display unit for displaying signals provided from the control unit.

6. The growth plate stimulation-type portable growth promotion apparatus according to claim 1, further comprising a first connection terminal provided on one side of the promoter body in order to connect the first input unit, the first display unit, the ultrasonic vibration generators, and the LED devices to an outside.

7. The growth plate stimulation-type portable growth promotion apparatus according to claim 6, further comprising a controller body including a second connection terminal connected to the first connection terminal using a connection cable; wherein the controller body comprises; a power supply device provided therein; a control unit connected to the power supply device, and connected to the first input unit, the first display unit, the two-phase ultrasonic vibration generators and the LED devices of the promoter body through the second connection terminal; and a second input unit and a second display unit connected to the control unit.

8. The growth plate stimulation-type portable growth promotion apparatus according to claim 7, wherein the first input unit is an input unit for inputting a signal used to control a strength of each of the two-phase ultrasonic vibration generators and each of the LED devices; wherein the first display unit is a display unit for displaying operational time of the growth plate stimulation-type portable growth promotion apparatus; wherein the second input unit is an input unit for inputting a signal used to control an operational mode of the growth plate stimulation-type portable growth promotion apparatus; and wherein the second display unit is a display unit for displaying signals provided from the control unit.

\* \* \* \* \*